(12) United States Patent
Philipp et al.

(10) Patent No.: US 8,165,670 B2
(45) Date of Patent: Apr. 24, 2012

(54) STIMULATION SYSTEM FOR TREATMENT OF DYSPHAGIAS

(75) Inventors: Jens Philipp, Berlin (DE); Dirk Kautz, Mahlow (DE); Hubertus Feussner, Munich (DE)

(73) Assignee: Biotronik CRM Patent AG, Baar (CH)

( * ) Notice: Subject to any disclaimer, the term of this patent is extended or adjusted under 35 U.S.C. 154(b) by 452 days.

(21) Appl. No.: 12/190,476

(22) Filed: Aug. 12, 2008

(65) Prior Publication Data

US 2009/0048645 A1    Feb. 19, 2009

(30) Foreign Application Priority Data

Aug. 16, 2007    (DE) .......................... 10 2007 038 816

(51) Int. Cl.
*A61N 1/00*    (2006.01)

(52) U.S. Cl. ............................................. 607/2; 607/48

(58) Field of Classification Search ................ 607/1–76, 607/115–154

See application file for complete search history.

(56) References Cited

U.S. PATENT DOCUMENTS

| | | | |
|---|---|---|---|
| 5,725,564 A * | 3/1998 | Freed et al. .................. | 607/72 |
| 5,891,185 A | 4/1999 | Freed et al. | |
| 7,606,623 B2 * | 10/2009 | Ludlow et al. ................ | 607/62 |
| 7,734,351 B2 * | 6/2010 | Testerman et al. ............ | 607/48 |
| 2003/0078521 A1 | 4/2003 | Robbins et al. | |
| 2007/0066995 A1 * | 3/2007 | Strother et al. ................ | 607/2 |
| 2008/0147141 A1 * | 6/2008 | Testerman et al. ............ | 607/48 |

FOREIGN PATENT DOCUMENTS

WO    2007005582    1/2007

OTHER PUBLICATIONS

European Search Report, dated Dec. 17, 2008, 3 pages.
Burnett et al. "Self-triggered functional electrical stimulation during swallowing," Journal of Neurophysiology, American Physiological Society, vol. 94, No. 6, Aug. 17, 2005, pp. 4011-4018.

* cited by examiner

*Primary Examiner* — Niketa Patel
*Assistant Examiner* — Mallika Fairchild
(74) *Attorney, Agent, or Firm* — ARC IP Law PC; Joseph Mayo

(57) ABSTRACT

Stimulation system, comprising an implantable stimulation device (60), at least one implantable stimulation electrode (70) and at least one initializing sensor (40), whereby the initializing sensor (40) is configured to detect in the implanted state a voluntarily controlled muscle movement, a voluntarily induced brainwave or a voluntarily generated nerve pulse of a patient during the initial phase of a swallowing process and to generate a sensor signal in response thereto either continuously or in a clocked cycle or in response to the preceding and to send this signal to the stimulation device (60), and whereby the stimulation device (60) is configured to trigger the delivery of a stimulation pulse via the stimulation electrode (70) in response to such a sensor signal of the initializing sensor (40) which is based on a voluntarily initiated swallowing process.

14 Claims, 2 Drawing Sheets

STIMULATION SYSTEM FOR TREATMENT OF DYSPHAGIAS

This application takes priority from German Patent Application DE 10 2007 038 816.2, filed 16 Aug. 2007, the specification of which is hereby incorporated herein by reference.

BACKGROUND OF THE INVENTION

1. Field of the Invention

The invention relates to an implantable medical system, in particular a system for triggering the act of swallowing in swallowing disorders, so-called cervical dysphagia.

2. Description of the Related Art

Swallowing disorders occur, for example, when food is not correctly directed into the esophagus after the onset of the voluntarily initiated swallowing process because the sphincter muscle at the point of intersection between the trachea and the esophagus (the esophageal sphincter) is inactivated inadequately or not at all. This dysphagia may be caused by damage to certain areas of the brain, for example, or by the connecting nerves and is often a result of a stroke.

Dysphagias are among the physical impairments that have an especially negative effect on a patient's quality of life. In addition, cervical dysphagia is a concrete health threat, in particular due to the sequelae, such as malnutrition, dehydration, respiratory problems, dependency on tubal nutrition and/or tracheal cannulas, death and the high cost of the health care system.

Another risk is that unchewed food and overly large bites of food "remain stuck in the throat" and may even lead to an obstruction of the respiratory tract. This may come about due to the fact that the food slips into the trachea instead of entering the esophagus when the esophageal sphincter is activated inadequately or not at all. The result may be respiratory arrest and cardiac arrest.

This is also illustrated in particular by the fact that dysphagias are one of the most common causes of death of patients within the first year after a stroke.

Due to the increasing life expectancy and the associated neurological diseases (strokes) and oncological diseases (cancer) in the head and neck area, there has been a constant increase in the number of patients suffering from swallowing disorders (dysphagias).

In a stroke (incidence 24 of 100,000, prevalence 1,200 of 100,000 in western industrial nations) more than 50% of those affected suffer from clinically relevant swallowing disorders during the acute phase. Of this 50%, approximately half die or recover adequately, so that approximately 25% of stroke patients have chronic dysphagia.

A second group which is constantly increasing includes the area of the geriatric population. Dysphagias occur in 30-60% of elderly residents of nursing homes. Dysphagia almost always occurs with advanced dementia. Numerous other diseases and frequently neurological diseases are associated with dysphagias. For example, approximately 40-50% of patients with Parkinson's disease (prevalence 300-1,000/100,000) suffer from dysphagias, and approximately 30-40% of patients with multiple sclerosis (prevalence 100/100,000) suffer from dysphagias.

Exogenous systems known from the state of the art for treatment of cervical dysphagia include the VITALSTIM® system, which provides neuromuscular electric stimulation and stimulates the area of the anterior neck region from the outside during the swallowing process to trigger a contraction of the swallowing musculature.

This stimulation of the swallowing musculature is, however, aimed only at activation of individual or multiple muscles but not at initiation of the entire swallowing process. Results of studies of such systems have been disappointing so far.

Investigations of electric stimulation in the area of the throat, the palatopharyngeal arch and in the area of the neck with a different frequency and intensity have been and are being conducted and our studies with regard to the efficacy thereof, i.e., the positive influence on relevant swallowing parameters, have been tested but have not yet led to a system that enables a patient to have a virtually normal and natural swallowing action.

BRIEF SUMMARY OF THE INVENTION

The object of the present invention is thus to provide a system that overcomes the aforementioned disadvantages.

This aforementioned object is achieved according to this invention by a fully implantable stimulation system, which is triggered by a voluntary muscle movement, a voluntarily induced brainwave or a voluntarily generated nerve pulse in a patient during the initial phase of a swallowing process and thereby causes stimulation of the reflexive sequence of the swallowing process.

The term "voluntarily induced brainwave" is understood to refer to those measurable electric activities of the brain that are "trainable" and can be consciously triggered by a patient to initiate a swallowing process. The term "voluntarily induced nerve pulse" is understood to refer to such measurable nerve pulses which are also "trainable" and can be consciously triggered by a patient. Similarly, the term "voluntary muscle movement" refers to muscle movements that can be controlled voluntarily.

The inventive stimulation system includes an implantable stimulation device, at least one implantable stimulation electrode and at least one initializing sensor.

The initializing sensor is designed to detect a voluntarily controlled muscle movement, a voluntarily induced brainwave or a voluntarily generated nerve pulse of a patient during the initial phase of a swallowing process, then to generate a sensor signal continuously, in a cycle or in response to the former and to forward this signal to the stimulation device. The stimulation device is in turn designed to trigger delivery of a stimulation pulse via the stimulation electrode in the case of such a sensor signal of the initializing sensor representing a voluntary initialization of the swallowing process.

A signal that triggers delivery of a stimulation pulse is also referred to in the context of this invention as a triggering sensor signal and/or trigger signal. For such an embodiment of the invention in which the initializing sensor generates a sensor signal exclusively in the case of an actual muscle movement, a brainwave actually induced voluntarily or a nerve pulse actually generated voluntarily during the initial phase of a swallowing process, and delivers this sensor signal to the stimulation device, the sensor signal is a trigger signal accordingly. For such an embodiment, however, in which the initializing sensor delivers a sensor signal continuously to the stimulation device, the triggering sensor signals and/or trigger signals must first be "filtered out" from this signal—as explained in greater detail below—in the course of signal processing.

When implanted in a patient's body, a patient's reflexive swallowing action is triggered with the help of the inventive stimulation system by a voluntarily controlled muscle movement, a voluntarily induced brainwave or a voluntarily generated nerve pulse for initiating a swallowing process.

The initializing sensor—hereinafter also referred to as the sensor—is preferably designed as a pressure sensor and especially preferably is a pressure sensor for an oriented pressure measurement in the range of 30 to 500 mmHg with a resolution of approx. delta 5 to 10 mmHg and a frequency of 2 to 5 Hz and is especially preferably designed to detect pressure of the tongue and/or a bolus of food against a patient's palate and then deliver a sensor signal to the stimulation device.

In principle, however, any sensor that is capable of detecting a voluntarily controlled muscle movement, a voluntarily induced brainwave or a voluntarily generated nerve pulse is suitable for this purpose. Examples of such initializing sensors include oculometers, electro-oculography (EOG) sensors, electroencephalography (EEG) sensors or pressure sensors that can detect a pressure applied externally to a patient's cheek. Depending on the embodiment and the desired detection site, such sensors are designed to be arranged on the surface of a patient's body or implanted in a patient's body. They preferably have suitable means for attaching them in or to a patient's body.

A predefined pressure of the tongue against the hard palate especially preferably serves as the sensor signal for stimulation of the reflexive swallowing process. A sensor detecting such a pressure is attached in or to the palate.

For transmission of the sensor signal to the stimulation device, the sensor is preferably electrically connected to the stimulation device via a sensor electrode line.

According to another variant of the embodiment, however, the sensor has its own power supply and is designed for wirelessly transmitting a sensor signal to the stimulation device.

To prevent a sensor signal from triggering an unwanted swallowing process and/or to decide whether an incoming sensor signal can be attributed to a voluntarily controlled muscle movement, a voluntarily induced brainwave or a voluntarily generated nerve pulse during the initial phase of a swallowing process, the sensor and/or the stimulation device according to a preferred embodiment has a signal processing unit for "filtering out" of the sensor signal and/or the sensor signals only those which can actually be attributed to a voluntary initiation of a swallowing process.

The signal processing is preferably designed to perform such filtering with the help of one or more threshold values and/or with the help of a required chronological characteristic of the sensor signal and thereby prevent unwanted stimulation of the reflexive sequence of the swallowing process.

Preferably a characteristic pressure profile on a patient's palate, especially preferably a patient-individual pressure profile is used as the comparative value and/or as the comparative signal. According to additional embodiments, a pressure curve that is individual for the patient serves as the comparative value or comparative signal characteristic in the area of a muscle, a patient-individual sequence of muscle movements, a patient-individual brainwave profile or a patient-individual nerve pulse sequence during the initial phase of a swallowing process serves to process and analyze the sensor signal.

After receiving the sensor signal and after processing the sensor signal, if necessary, the stimulation device in the implanted state delivers one or more stimulation pulses via the stimulation electrode(s) as needed to preferably one superior laryngeal nerve or to both superior laryngeal nerves (which are opposite one another), thereby triggering the swallowing process. The entire oropharyngeal swallowing process is initiated by stimulation of these nerves.

To be able to implant the stimulation device in a patient's body even at a distance from the site of the stimulation electrode(s), the stimulation device preferably has a connection for a stimulation electrode line or the stimulation device is fixedly connected to such an electrode line. A stimulation pulse generated in the event of treatment is sent over the electrode line to the stimulation electrode and is thereby delivered.

According to another variant of the embodiment, the stimulation system has at least two stimulation electrodes, each being connected or connectable to the stimulation device or to one of its components, preferably via its own stimulation electrode line for each.

According to another variant of the embodiment, the stimulation electrode has its own power supply and a wireless data transmission unit, preferably with a transmitter and a receiver, and is designed for receiving stimulation pulses.

Through electric stimulation of a nerve, the superior laryngeal nerve, a central pattern generator (CPG) for swallowing is activated in the patient's brain by the electric stimulation in the event of an application and coordinates in a suitable manner the movement of the individual swallowing muscles. Unilateral stimulation of the superior laryngeal nerve is also sufficient to trigger a swallowing process that takes place in an orderly manner in space and time.

Other suitable stimulation sites may include other nerves or areas in the brain. According to the desired stimulation site, the inventive stimulation system is equipped with at least a suitably adapted stimulation electrode. According to one variant of the embodiment, the electrode is formed by a helical electrode.

The stimulation device itself preferably has a pulse shaper, a computer unit and a memory and especially preferably also has its own power supply. The memory of the stimulation device is designed to store parameters with the help of which the computer unit calculates a preferably patient-individual stimulation and/or stimulation sequence and can calculate and induce a corresponding pulse generation by the pulse shaper. The corresponding parameters preferably contain information with the help of which a time lag between the sensor signal to be triggered and the delivery of the stimulation signal and/or the stimulation frequency and/or the stimulation type (controlled by electric current or voltage) and/or the intensity of the stimulation pulses and/or the duration of a stimulation cycle and/or the frequency of the stimulation cycles can be determined and can be generated by the pulse shaper.

If the stimulation device is provided for processing the sensor signal as described above, then in this case the computer unit is preferably designed to assume this task.

According to an especially preferred variant of the embodiment, the stimulation device is also designed to be able to perform an automatic adaptation of the stimulation parameters.

According to another variant of the embodiment or in combination with the variant of the embodiment for independent adaptation of the stimulation parameters, the stimulation system has, in addition to the initializing sensor, at least one additional sensor which is designed to detect successful stimulation of the reflexive swallowing process.

According to another variant of the embodiment, the stimulation device has a wireless data transmission unit, which is designed to be able to receive parameters sent by an external programming unit and provided for storage in the memory.

Accordingly, another aspect of the present invention is an external programming device, which is equipped with at least one input interface and one wireless data transmission unit. The data transmission unit of the programming device is tuned to the corresponding wireless transmission unit of the stimulation device. Not only is the external programming device preferably designed to transmit data to the stimulation device, but also the data transmission units of the programming device and of the stimulation device are designed for bidirectional data transmission. In this case, the external programming device preferably also has a parameter analyzing unit, which is designed to be able to analyze the data transmitted by the stimulation device.

BRIEF DESCRIPTION OF THE DRAWINGS

These and additional aspects of the present invention should now be explained in greater detail on the basis of the following description of the figures, in which.

DETAILED DESCRIPTION OF THE INVENTION

Figure 1:
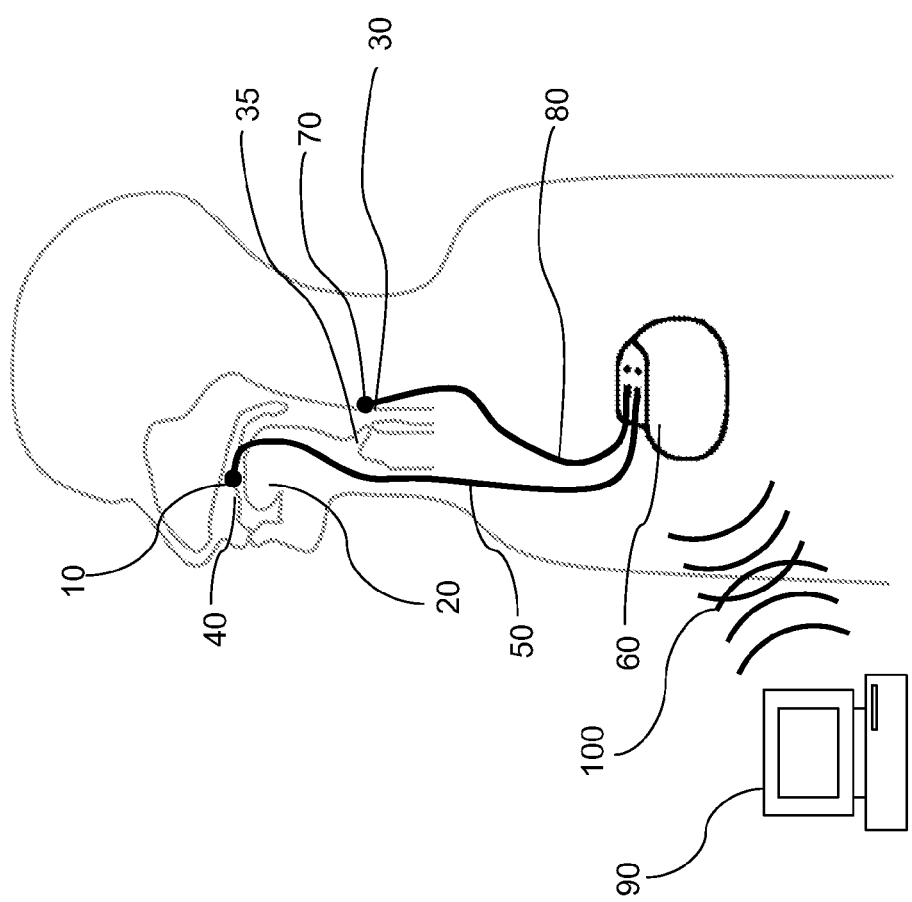
FIG. 1 shows an exemplary arrangement of the stimulation device, sensor and stimulation electrode in the human body.

FIG. 1 shows one possible arrangement of the inventive stimulation system in a patient's body. The stimulation system according to FIG. 1 has a stimulation device 60, which is electrically connected to the sensor 40 via a sensor electrode line 50 and supplies it with energy. In addition, the stimulation device 60 is connected to a stimulation electrode 70 via a stimulation electrode line 80.

In the simplest case, the sensor 40 is a switch that forwards a sensor signal to the stimulation device 60 only when activated. In such a case, each sensor signal incoming to the stimulation device 60 is a triggering sensor signal, i.e., a trigger signal, because it is always attributed to a voluntarily controlled muscle movement, a voluntarily induced cerebral electric current or a voluntarily generated nerve pulse for initiation of a swallowing process. According to the variant of the embodiment depicted here, however, it is a pressure sensor whose sensor signal is relayed to the stimulation device 60 via a sensor electrode line 50 either continuously or in a clocked cycle and is processed there.

The stimulation device 60 analyzes the signals of the sensor 40 and recognizes from them the pressure of the tongue 20 on the palate 10, which is representative for the onset of a swallowing process.

Then the stimulation device 60 generates a stimulation pulse and outputs it via the stimulation electrode line 80 to the stimulation electrode 70. In this case, the stimulation electrode 70 is implanted in a patient's body, so that it stimulates the superior laryngeal nerve 30.

This superior laryngeal nerve 30 is stimulated by the stimulation device 60 via the stimulation electrode 70 and thereby activates the sphincter muscle 35.

The start of stimulation of the superior laryngeal nerve 30 occurs after an adjustable time lag (e.g., 100 ms) with respect to receiving the triggering sensor signal.

In addition to the implantable stimulation system, FIG. 1 also illustrates an external programming device 90 as an additional aspect of the present invention.

The programming device 90 is designed to communicate with the stimulation device 60 unidirectionally and/or bidirectionally over a wireless communication link 100.

Figure 2:
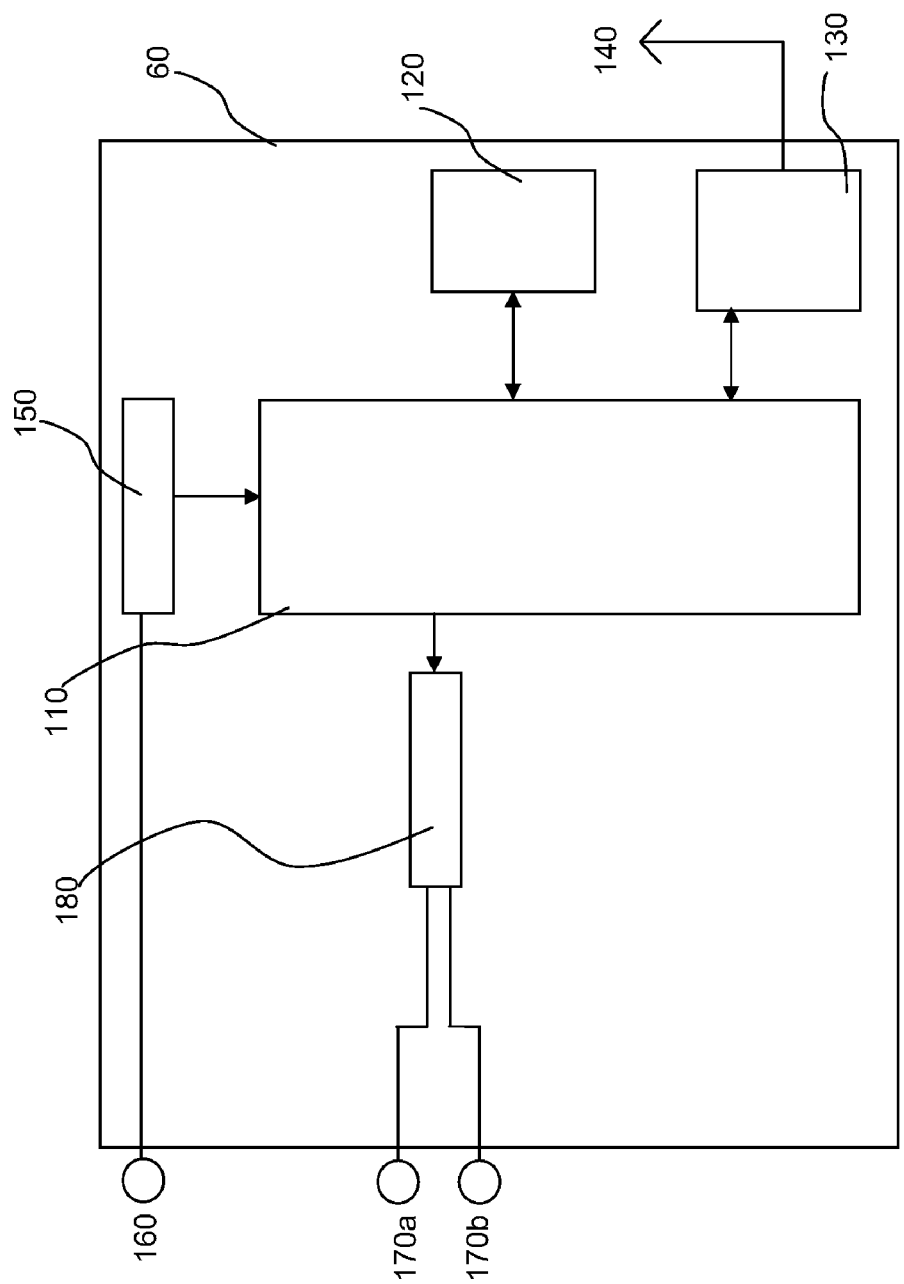
FIG. 2 shows a block diagram of a variant of the embodiment of the inventive stimulation device.

The communication 100 between the stimulation device 60 and the programming device 90 takes place via a wireless data transmission unit 130, which is shown in FIG. 2 and which receives and sends signals and/or data from programming unit 90 via an antenna 140 in case of need.

In this way, parameters of stimulation can be adjusted in the stimulation device 60 via the programming device 90. Stimulation parameters may include: time lag between the triggering sensor signal and delivery of the stimulation pulse, stimulation frequency, type of stimulation (controlled by current or voltage), intensity of the stimulation pulses, duration of a stimulation cycle, frequency of the stimulation cycles.

In another embodiment, the stimulation device 60 can also adjust these parameters automatically.

FIG. 2 shows the block diagram of a variant of the embodiment of stimulation device 60.

The stimulation device 60 contains a computer unit 110 which is designed to be able to store data and/or parameters in a memory 120 and retrieve them again. The parameters are values which define more specifically a stimulation pulse that is to be generated.

If, in event of treatment, the sensor signals recorded by the sensor 40 are sent to the stimulation device 60 over the electrode line 50, they are forwarded via the plug 160 to the signal processing unit 150, where they are processed and forwarded from there to the computer unit 110.

The sensor signal recorded is processed in the signal processing unit 150 with the help of various threshold values and is checked with regard to the presence of a voluntarily controlled muscle movement, a voluntarily induced brainwave or a voluntarily generated nerve pulse in the initial phase of the swallowing process. The processed sensor signal is then forwarded to the computer unit 110.

When an initial phase of a swallowing process occurs, the computer unit 110 utilizes the stimulation parameters stored in the memory 120 and/or calculates new suitable signal parameters and forwards them to a stimulation pulse shaper 180.

The stimulation pulse shaper 180 shapes suitable stimulation pulses according to the parameters.

The stimulation pulses are then forwarded to the stimulation electrode 70 via a plug 170a or 170b over the stimulation electrode line 80 and then sent on to the stimulation site 30.

In the case of bipolar stimulation, the pulse is directed via the two plugs 170a and 170b and via the stimulation electrode line 80 to the stimulation electrode 70 and further to the site of stimulation 30.

If the treatment is unipolar, then there is one pole 70 at the end of the electrode line 80 from which a stimulation pulse is delivered to the housing of the implant in the event of treatment.

If stimulation is bipolar, then there are two poles 70 at the end of the electrode line 80 (not visible in FIG. 1) between which the stimulation pulse is delivered.

The stimulation pulses are preferably controlled by current, i.e., the amperage of the stimulation pulses is adjustable.

In another embodiment, the stimulation pulses are controlled by voltage, i.e. the height of the voltage of the stimulation pulses is adjustable.

What is claimed is:

1. A stimulation system for treatment of dysphagias comprising:
    an implantable stimulation device (60);
    at least one implantable stimulation electrode (70);
    at least one initializing sensor (40) configured to be attached in or to a palate of a patient wherein said at least one initializing sensor is further configured to detect a swallowing process in the patient through detection of a pressure of a tongue against the palate of said patient, generate a sensor signal continuously, or in a clocked cycle and send the sensor signal to the implantable stimulation device (60); and, wherein the implantable stimulation device (60) comprises a computer unit (110) that is configured to filter out of said sensor signal, a filtered sensor signal, that represents only signals which can be attributed to a voluntary initiation of said swallowing process through comparison of a chronological characteristic of said sensor signal to a pressure profile or patient-individual pressure profile to prevent unwanted stimulation of said swallowing process;

trigger a delivery of a stimulation pulse via the at least one implantable stimulation electrode (70) in response to the filtered sensor signal that represents a voluntary initiation of the swallowing process.

2. The stimulation system according to claim 1, wherein the implantable stimulation device (60) comprises a timer and is configured to induce the delivery of the stimulation pulse after a predetermined delay time after receipt of a triggering sensor signal.

3. The stimulation system according to claim 1, wherein the implantable stimulation device (60) is electrically connected to the at least one initializing sensor (40) via a sensor electrode line (50).

4. The stimulation system according to claim 1, wherein the at least one initializing sensor (40) comprises a power supply and is configured to allow wireless transmission of the sensor signal to the implantable stimulation device (60).

5. The stimulation system according to claim 1, wherein the at least one initializing sensor (40) is a pressure sensor and the sensor signal is processed in the at least one initializing sensor (40) itself.

6. The stimulation system according to claim 1, wherein the at least one initializing sensor (40) is a pressure sensor configured to deliver the sensor signal to the implantable stimulation device (60) wherein the implantable stimulation device (60) is configured to process the sensor signal of the at least one initializing sensor.

7. The stimulation system according to claim 1, wherein the at least one implantable stimulation electrode (70) is connected electrically to the implantable stimulation device (60) via a stimulation electrode line (80).

8. The stimulation system according to claim 1, wherein the at least one implantable stimulation electrode (70) comprises a power supply and is wirelessly connected to the implantable stimulation device (60).

9. The stimulation system according to claim 1, wherein the implantable stimulation device (60) has at least two stimulation electrodes (70) and/or at least two initializing sensors (40).

10. The stimulation system according to claim 1, wherein the implantable stimulation device (60) comprises:

a stimulation pulse shaper (180);

a memory (120) configured to store parameters for the computer unit to utilize; and, wherein the computer unit (110) is further configured to determine a time lag between a triggering sensor signal and the delivery of the stimulation pulse, and/or determine a stimulation frequency, and/or determine a type of stimulation, and/or determine a duration of a stimulation cycle, and/or determine a frequency of stimulation cycles, and induce a corresponding pulse generation by the stimulation pulse shaper (180).

11. The stimulation system according to claim 10, wherein the implantable stimulation device (60) further comprises a wireless data transmission unit (130), which is configured to receive parameters sent wirelessly via an external programming device (90) that are stored in the memory (120).

12. The stimulation system according to claim 1, wherein the implantable stimulation device (60) is configured to induce an automatic adjustment of stimulation parameters.

13. The stimulation system of claim 1 further comprising an external programming device (90) that comprises at least one input interface and a wireless data transmission unit, which is configured to transmit stimulation parameters wirelessly to the implantable stimulation device (60).

14. The stimulation system of claim 13 wherein the external programming device (90) comprises a wireless data receiving unit and a parameter analyzing unit, which is configured to receive and analyze the stimulation parameters transmitted wirelessly from the implantable stimulation device (60).

* * * * *